(12) United States Patent
Jones

(10) Patent No.: US 6,245,010 B1
(45) Date of Patent: Jun. 12, 2001

(54) RADIANT HEATER FOR INFANT WARMERS

(75) Inventor: Thomas C. Jones, Columbia, MD (US)

(73) Assignee: Datex-Ohmeda, Inc., Tewksbury, MA (US)

( * ) Notice: Subject to any disclaimer, the term of this patent is extended or adjusted under 35 U.S.C. 154(b) by 0 days.

(21) Appl. No.: 09/316,355

(22) Filed: May 21, 1999

(51) Int. Cl.[7] .............................. A61F 7/00; F24H 9/06; A61B 11/00
(52) U.S. Cl. ............................................................ 600/22
(58) Field of Search ........................ 600/21, 22; 607/88, 607/90

(56) References Cited

U.S. PATENT DOCUMENTS

| | | |
|---|---|---|
| 1,776,863 | 9/1930 | Maxson . |
| 1,817,027 | 8/1931 | Anderson . |
| 2,384,670 | 9/1945 | Fisher et al. . |
| 2,681,061 | 6/1954 | Modell . |
| 3,585,390 | 6/1971 | Ishikawa . |
| 4,731,714 | 3/1988 | Kelly et al. . |
| 4,809,677 | 3/1989 | Mackin et al. . |
| 5,474,517 | 12/1995 | Falk et al. . |
| 5,830,123 | * 11/1998 | Franz et al. . |
| 5,989,283 | * 11/1999 | Wilkens ................................. 607/88 |

FOREIGN PATENT DOCUMENTS

| | | |
|---|---|---|
| 785 969 | 11/1972 | (BE) . |
| 31 27 707 | 2/1983 | (DE) . |
| 0 832 668 | 1/1998 | (EP) . |

\* cited by examiner

*Primary Examiner*—Samuel G. Gilbert
(74) *Attorney, Agent, or Firm*—Roger M. Rathbun

(57) ABSTRACT

An infant care center or infant care warmer having as it source of heat, a radiant heater that includes a reflector in the shape of a quadratic surface of revolution consisting of a paraboloid, an ellipsoid or a hyperboloid. The shape allows the heater to be positioned at the head of the infant care apparatus and out of the way of the attending personnel and yet deliver sufficient heat to provide warmth to the infant. An infrared energy emitter is positioned at substantially the focal point of the geometric configuration of the reflector to provide radiant energy to be reflected toward an infant resting on a planar surface underneath the heater. While out of the way of the infant and the attending personnel, the radiant heater provides a generally uniform footprint of heat to the infant.

14 Claims, 6 Drawing Sheets

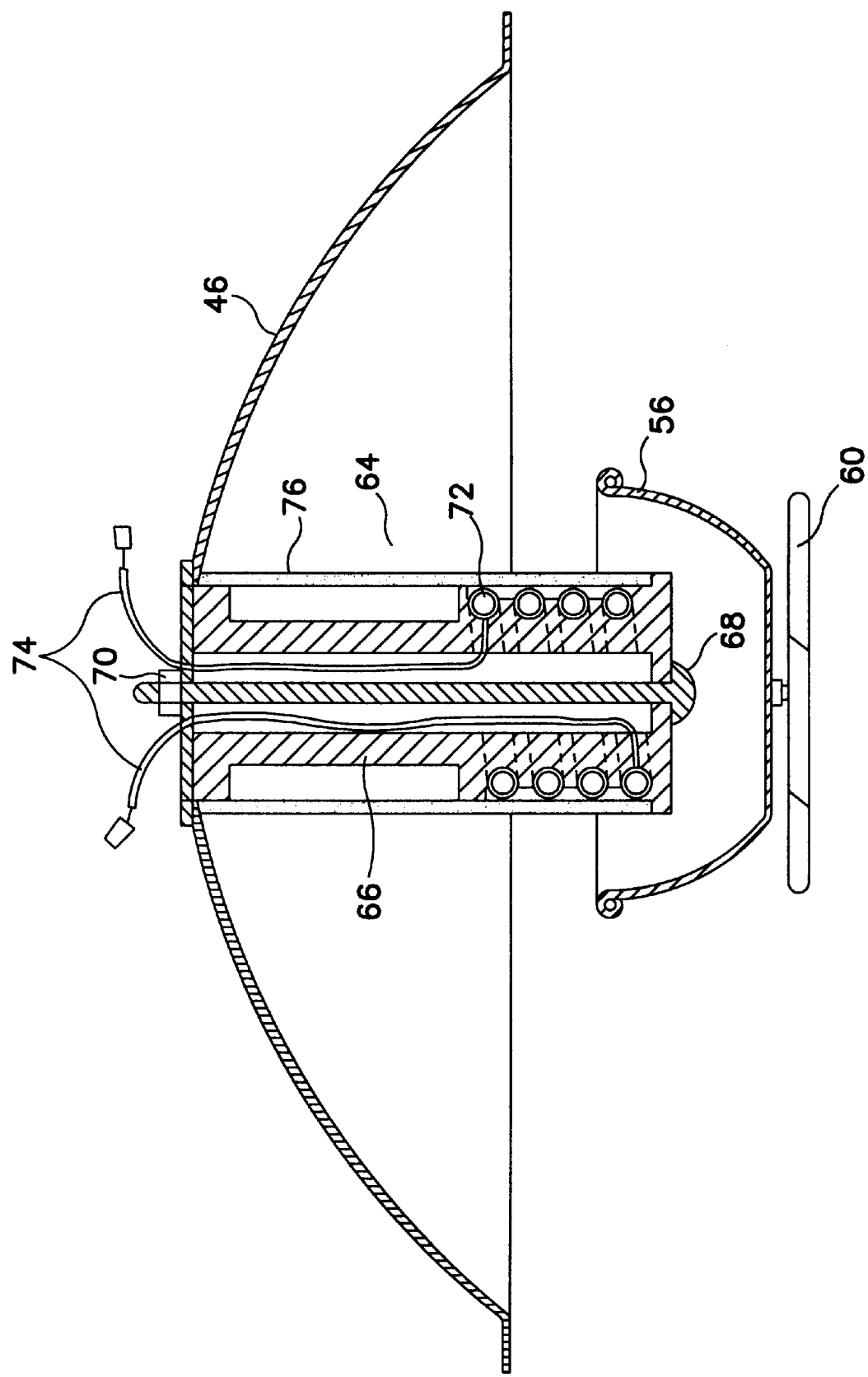

RADIANT HEATER FOR INFANT WARMERS

BACKGROUND OF THE INVENTION

The present invention relates to an infant care apparatus of the type that provides a support or bed for the infant as well as includes an overhead heating unit that directs infrared heat toward the infant for heating that infant.

In such infant care centers one common type of heater that is used is generally of a radiant type including one or more cylindrical heaters that are positioned above the infant. Typically, cylindrical radiant heating element consists of a resistance wire coil insulated with a compacted insulation within a metallic tubular sheath. Alternately, the cylindrical radiant heating element may consist of a resistance wire coil contained within a quartz tube. In general, these heating elements are about 18 inches long and are about ½ inch in diameter.

Such infant care heaters also require a reflector since the heat needs to be directed toward the infant and the cylindrical heater emits infrared radiation in a full 360 degrees around its cylindrical length, as well as from its ends. One typical reflector is a metallic reflector that encloses the upper surface of the cylindrical heating element and is formed as an elongated reflector having its lateral cross section in the shape of a parabola to direct the radiation downwardly toward the infant. Such reflectors are cumbersome, and need considerable support in order to be retained in a sturdy position above the infant. Also, in the case where the heating element includes a quartz tube as the envelope, that quartz protective tube surrounding the resistance wire also requires protection to prevent breakage since, obviously, the breakage of the quartz envelope could cause harm to the patient or surrounding personnel.

One of the other deficiencies of such current heaters is, however, the very physical size of an elongated shaped heater that takes up considerable space directly over the infant. Obviously, since one of the advantages of an infant warmer is to be able to perform functions on the infant while positioned on the infant care apparatus, the presence of an elongated heater is a inconvenience and interferes with the administration of such procedures on the infant. Thus, the present heating units are relatively cumbersome and large and tend to be positioned at a focus point that directly interferes with the vision of the personnel attending to the infant or create a physical obstruction to such personnel.

Accordingly, the present heater units are generally difficult to work around and, at times, must be moved out of the way when personnel are attending to the infant such as when X-rays are being taken of the infant. In all, the long, cylindrical heating elements with their elongated reflectors create considerable inconvenience to the personnel attending to an infant.

An infant warming apparatus has been disclosed that does position the heater out of the way of the attending personnel, that of U.S. Pat. No. 5,474,517 to Falk et al, however, that Falk et al heater utilizes a special infrared emitter in order to carry out its operation. In addition, as noted in the Falk et al patent there is no reflector even required in order to provide the heat to the infant and thus Falk et al did not consider any particular shape of reflector in the apparatus.

It would be preferred to use a normal infrared emitter with a reflector located out of the way of normal access to the infant, however, with an infant warmer, it is very important that by relocating the heater to a differing location, not directly over the infant, that the overall heat provided to the infant not become non-uniform.

Obviously, it is important in the warming of an infant that the pattern of the heat directed on to the infant be uniform so that the infant is not being warmed excessively in one body location while realizing insufficient warmth in another body location. That is, while it is an advantage to relocate the heater to a position not directly over the infant, such a location has been difficult to achieve in infant care apparatus due to the need to have a uniform heat pattern on a planar surface underlying the infant and it has been thought that the off center location of an infant heater would prevent the obtaining of uniformity in the heat to the infant.

SUMMARY OF THE INVENTION

The infant care apparatus of the present invention includes a heater assembly that overcomes the foregoing problems and which employs a unique infrared heater system for the application of heat to an infant.

In particular, the present heater for an infant care apparatus provides an infrared emitter that has a reflector formed in a particular geometric shape where that 3-dimensional geometric shape has one focal point or two focal points. The infrared emitter is, to the extent possible, a point source of the infrared radiation and that radiation is reflected by a specially formed surface such that the infrared radiation is directed fairly uniformly on to a planar surface on which the infant is positioned.

The configuration of the reflector is a geometric shape having a surface whose equation is a quadratic in the variable of x, y and z, and, more specifically, the geometric surface is selected from the group consisting of an ellipsoid, a paraboloid and a hyperboloid. In the case of the paraboloid, the infrared emitter is located at or near the focal point of that geometric shape. In the case of the hyperboloid and the ellipsoid, the infrared emitter is placed near the focal point nearest the reflector for those geometric shapes. As an added feature, the reflective surface of the reflector has a specially prepared surface to enhance the reflecting of the infrared radiation in a uniform pattern upon the infant.

Accordingly, it has been found possible to use a particular shape or shapes of the heater reflector and to position the infrared emitter relative to that reflector such that the radiant heater assembly may be positioned at a greater vertical and horizontal distance from the center of the infant's bed than typical infant care heaters and yet provide a sufficiently uniform distribution of radiant heat over the infant bed.

As such, the specially shaped infrared heater is uniquely suitable for the heating of infants in an infant care center since the unit can be positioned out of the way of the attending personnel and thus not inconvenient to the working by that personnel upon the infant and yet provide an even distribution of heat on a planar surface.

Through the use of the particular shaped reflector, it is possible in an infant warming apparatus to position the heater at one side of the planar surface and direct that radiation upon the infant. In the preferred embodiment, the planar surface is substantially rectangular with the head and feet of the infant at the shorter of the opposing sides and the radiant heater is positioned along and above one of those short sides.

These and other characteristics of the present invention will become apparent through reference to the following detailed description of the preferred embodiment and accompanying drawings.

BRIEF DESCRIPTION OF THE DRAWINGS

FIG. 4 is a cross sectional view of an alternate infrared emitter that can be used with the present invention.

DESCRIPTION OF THE PREFERRED EMBODIMENT

Figure 1:
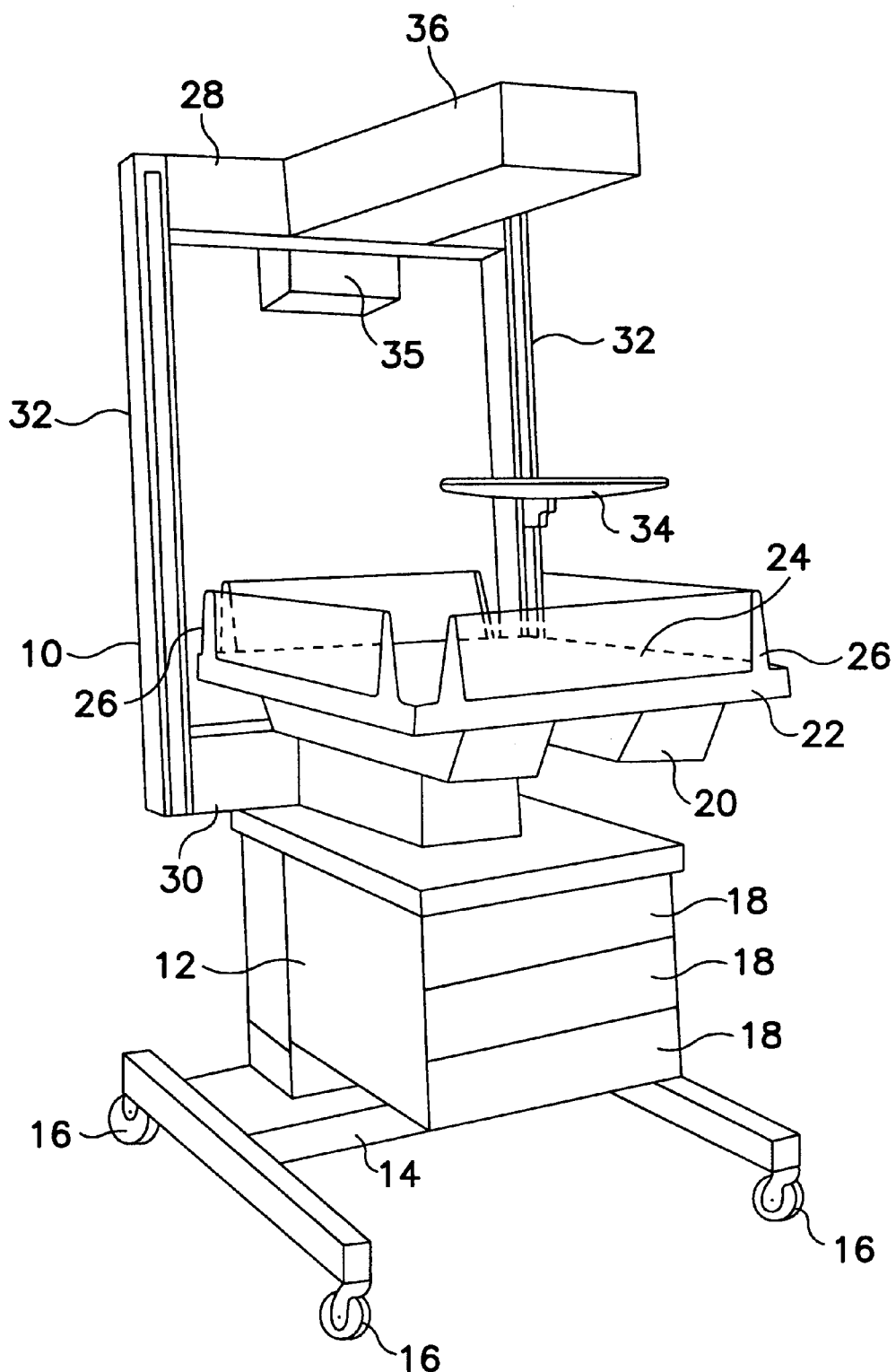
FIG. 1 is an isometric view of a typical prior art infant care center having a conventional heater.

Referring now to FIG. 1, there is shown an isometric view of a typical prior art infant care center having a conventional heater mechanism. As shown, the infant care center includes a frame 10 that provides a free standing unit for the infant care center. The frame 10 is supported upon a cabinet 12 which, in turn, is mounted upon a base 14 having wheels 16 so that the infant care center is easily movable. The cabinet 12 may also include one or more drawers 18 for containing items for attending to the infant.

An infant pedestal 20 is mounted atop of the cabinet 12 and on which is located an infant bed 22 which underlies an infant positioned thereon. Pedestal 20 is the main support for infant bed 20. The infant bed 22 has a generally planar upper surface 24 with appropriate cushioning material for comfort of the infant and further may be surrounded by guards 26, generally of a clear plastic material, and which contain the infant on the upper surface 24. Generally, the guards 26 are removable and/or releasable for complete access to the infant.

Frame 10 includes upper and lower cross members 28 and 30, respectively, joining a pair of vertical struts 32 and which vertical struts 32 may provide a means of support for other structural parts such as a shelf 34.

Mounted on the upper cross member 28 may be a control module 35 for containing the various electrical controls to operate the care center. In addition, a heater 36 is mounted to the upper cross member 28. As will be noted, the location of the heater 36 is positioned to be directly above the infant bed 22. The heater 36 is focused so as to provide a footprint on and around the infant to optimize the amount of heat directed upon the infant. Various types of focusable heaters are available for such application, examples of which may be a Calrod tubular metallic focused heater of about 500–600 watts, or a corrugated foil heater. The heater 36 is conventionally linear with a length such that the footprint of heat at the infant bed 22 is generally rectangular.

Typically, the heater 36 is about 18 to 24 inches in length extending outwardly, cantilever fashion from the cross member 28 and will contain therein, the Calrod resistance heater. Also, the heater 36 includes an elongated metal reflector having a generally parabolic cross section that redirects the infrared radiation emanating in all directions from the Calrod resistance heater downwardly towards the infant bed 22. The parabolic reflector and Calrod heater are not shown but are conventional in such currently available infant care centers.

Figure 2:
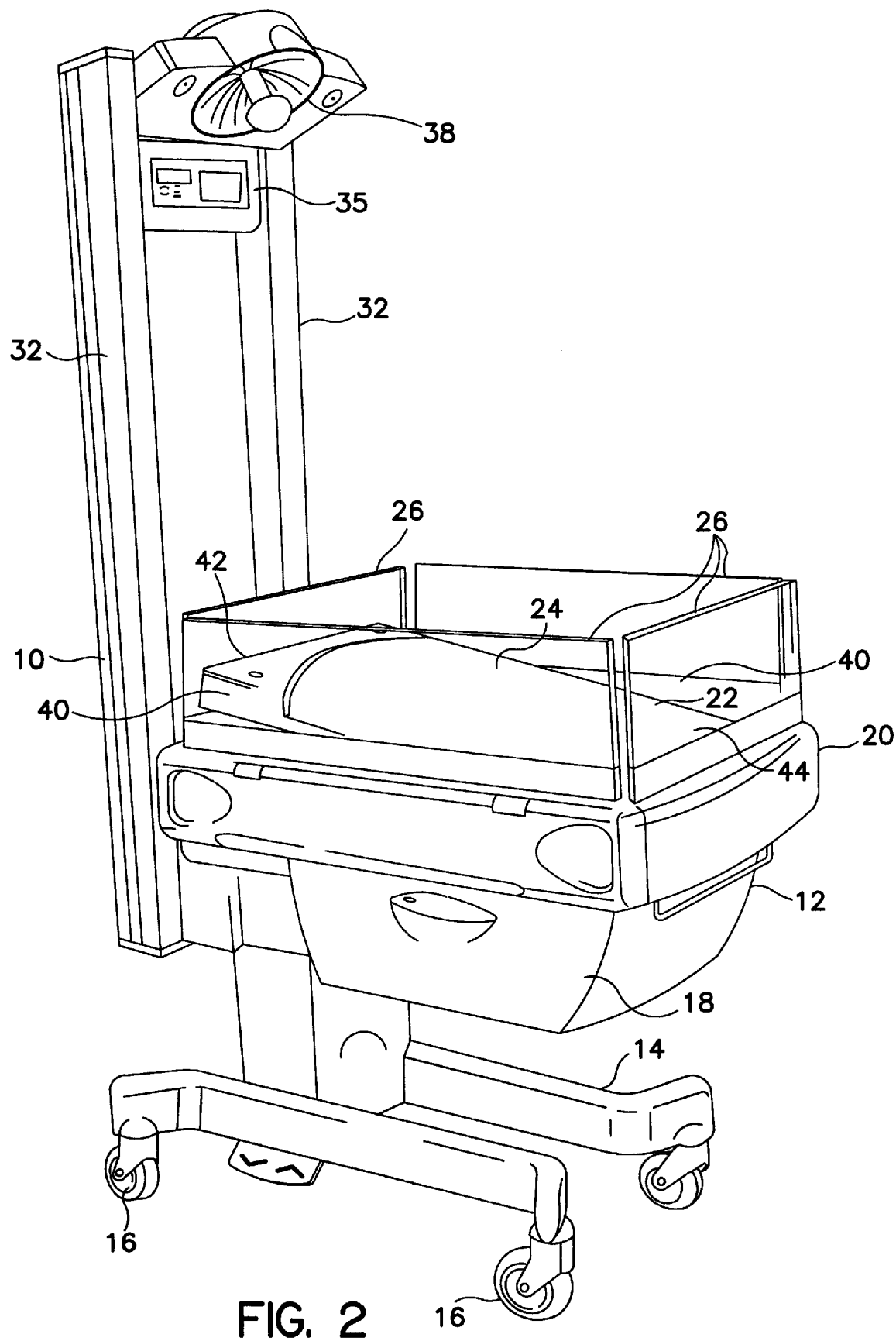
FIG. 2 is an isometric view of an infant care center having an infrared heater and reflector constructed in accordance with the present invention.

Turning now to FIG. 2, there is shown an isometric view of an infant care center utilizing a radiant heater 38 constructed in accordance with the present invention. In FIG. 2, the same identification numbers have been adopted for the corresponding components of the FIG. 1 prior art infant care apparatus even though there may be some differences in structure.

Accordingly, as may be seen in FIG. 2, the infant bed 22 is preferable a rectangular configuration having sides of differing lengths, it being seen that the side edges 40 of the infant bed 22 are longer than the top and bottom ends, respectively 42 and 44. As such, it is preferable that the infant be positioned on the infant bed 22 with the infant's head and feet generally along the long axis of the infant bed 22. As can also be seen, the positioning of the radiant heater 38 is such that it is adjacent the top end 42 of the infant bed 22 and is elevated so as to direct the radiant energy downwardly to impinge upon an infant positioned on the planar upper surface 24.

The location of the radiant heater 38 is such that it is out of the way of personnel attending to the infant and yet provides a heating effect to the infant in a uniform pattern and that pattern would not normally be anticipated by the offset location of the position of the radiant heater 38. The actual mounting of the radiant heater 38 to the upper cross member 28 may be in a variety of manners, however, in the preferred manner, there is a pivoted mounting such that the radiant heater 38 can be tilted to certain angles by the user when desired such as when heating a mother and her infant beside the infant bed. The pivoted mounting may have a means to return the heater to a pre-selected aim point such as the center of the infant bed 22.

Figure 3A:
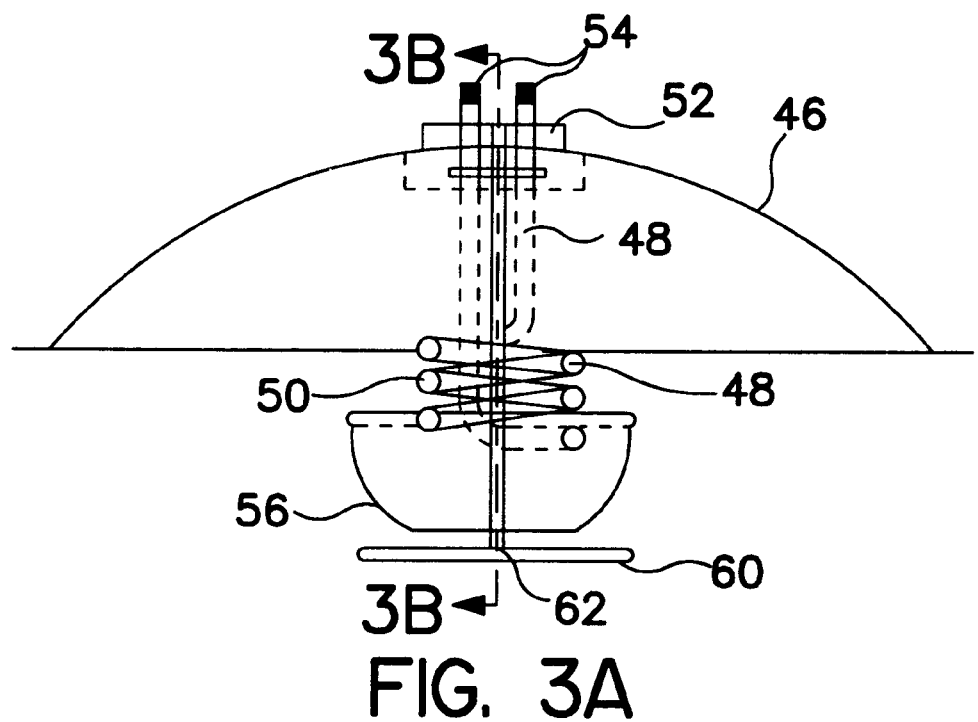
FIG. 3A is a side view of the heater constructed in accordance with the present invention and FIG. 3B is a cross sectional view taken along the lines BB of FIG. 3A
Figure 3B:
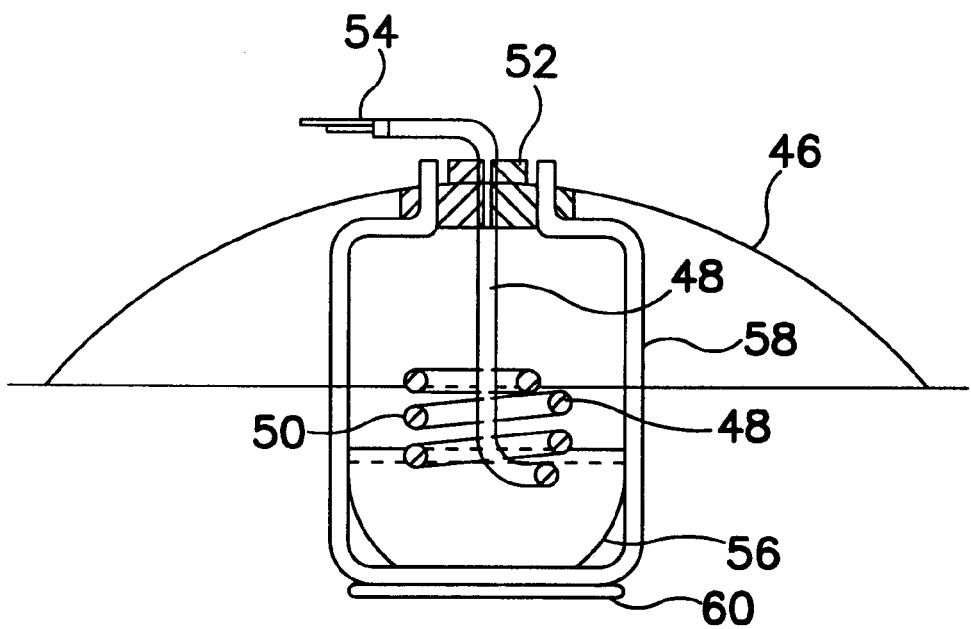
Figure 3C:
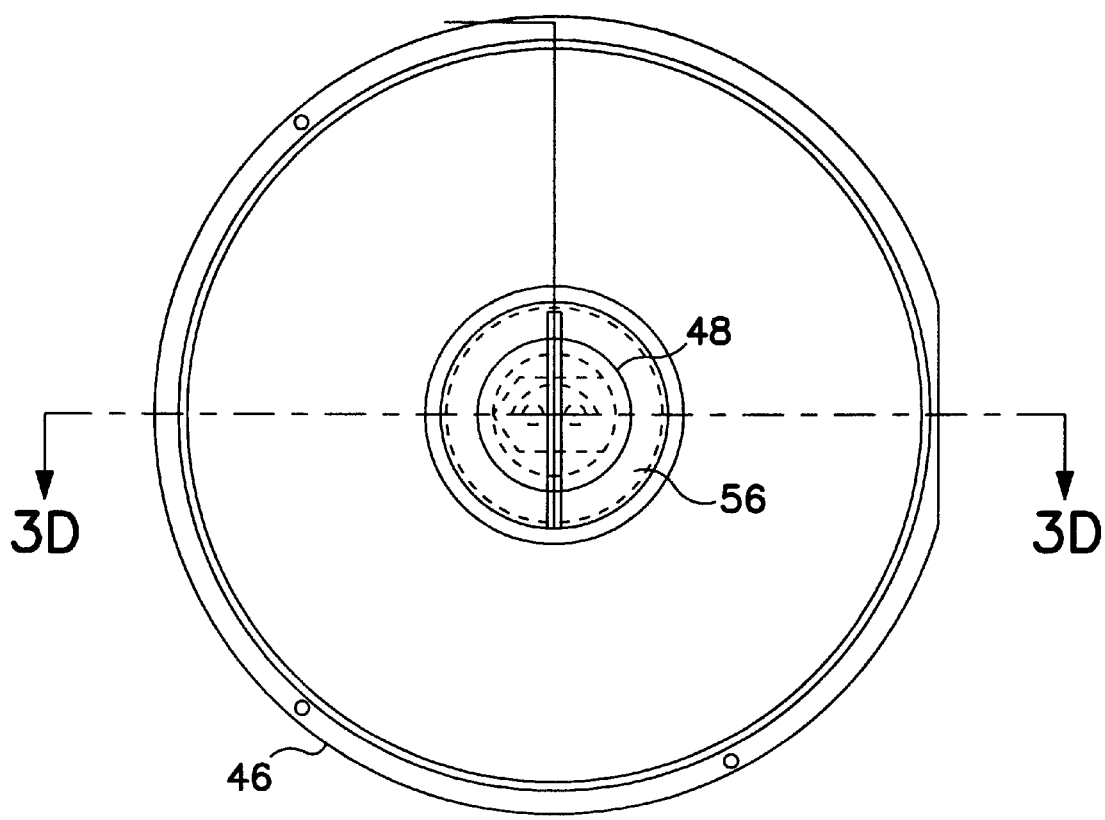
FIG. 3C is a bottom view of the heater of FIG. 3A
Figure 3D:
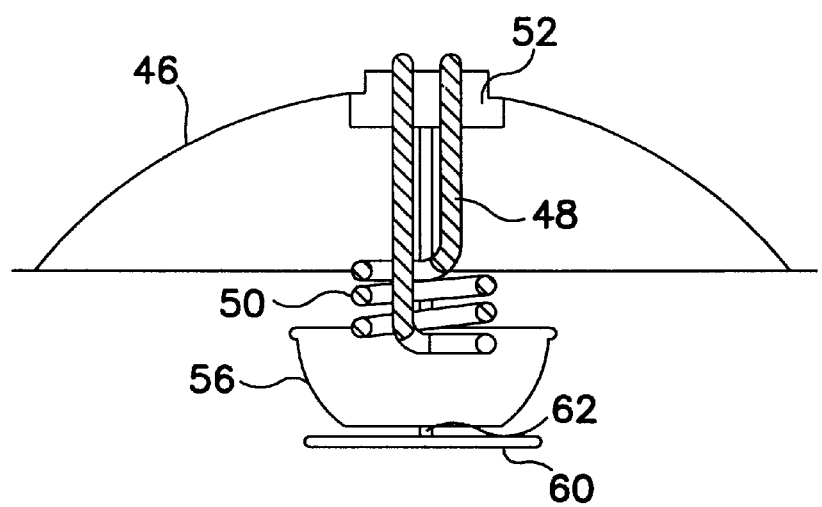
FIG. 3D is a cross sectional side view taken along the lines DD of FIG. 3C.

Turning now to FIGS. 3A–3D, there are shown figures of the radiant heater 38 constructed in accordance with the present invention. In particular, FIG. 3A is a side view of the radiant heater 38 while FIG. 3B is a side sectional view of the FIG. 3A embodiment taken along the lines B—B of FIG. 3A. FIG. 3C is a bottom view of the radiant heater 38 and FIG. 3D is a side cross sectional view taken along the lines D—D of FIG. 3C.

As can be seen, the radiant heater 38 comprises a reflector 46 that is designed so as to reflect radiant energy in the infrared spectrum toward than infant positioned on the planar upper surface 24 of FIGS. 1 and 2. The shape of the reflector 46, therefore, is specifically configured in the shape of a quadratic surface of revolution, specifically an ellipsoid, a paraboloid, or a hyperboloid. In the paraboloid, there is one focal point and at that point is located an infrared energy emitter 48. With the case of the hyperboloid and the ellipsoid, there are two focal and centered with respect to the axis of those two foci. As can be seen, the purpose of the location of the infrared energy emitter 48 is to provide the infrared energy that is then reflected by means of reflector 46 toward the planar upper surface 24.

In theory, therefore, the infrared energy emitter 48 should be at the focal point when there is only one focal point, or, alternatively, at the closest of the two focal points of the particular shape of the reflector 46 where there are two focal points. In practice, however, it is evident that the infrared energy emitter 48 is not truly a point source and, as such, cannot be located exactly at a point. Thus, there may be a need to be some adjustment of the exact position of the infrared energy emitter 48 in order to fine tune the footprint of the infrared energy as it impinges upon the planar upper surface 24.

In the preferred embodiment, the reflective surface of the reflector 46 is treated so as to maintain its reflectivity. The reflector itself can preferably be formed of aluminum and have coating of a clear protective material so that the reflector 46 does not lose its infrared reflectivity over time.

The infrared energy emitter 48 itself is preferably in the form of a coil 50 that, as explained, is substantially located at the desired point of the particular geometric shape that is used to form the reflector 46. It is important to make the coil 50 as small as possible to attempt to approach a point source, yet, of course, be within the constraints of the materials and be capable of supplying the amount of radiant energy required to maintain the infant at the desired temperature. Accordingly, as a preferred emitter, the infrared energy emitter 48 is formed as a tubular heater comprising a coiled resistance wire embedded within an insulating material such as a magnesium oxide and surrounded by a metal sheath. It has been found that such infrared energy emitter can supply adequate radiant energy and yet be sufficiently strong to be formed in a relatively tight coil.

The infrared energy emitter 48 is suspended within the reflector 46 by means of an insulator 52 that is affixed to the center of the reflector 46 to allow the coil 50 to be positioned substantially at the focal point of the geometric shape of reflector 46. External of the reflector 46, the infrared energy emitter 48 terminates in a pair of connectors 54 for connection to a suitable energy source to power the infrared energy emitter 48. A deflector 56 is also provided intermediate the coil 50 and the planar upper surface 24 (FIGS. 1 and 2) such that certain infrared energy emitted by infrared energy emitter 48 is deflected backwardly away from an infant on the planar upper surface 24 toward reflector 46. Thus, some of the radiant energy that would normally be directly radiated towards an infant is, instead, blocked by the deflector 56 and redirected to the reflector 46 where it is reflected towards that infant.

In the preferred embodiment, the deflector 56 is in the shape of a hemisphere with a truncated end and the deflector 56 actually encloses the lower section of the coil 50. The use of the deflector 56 limits the direct radiant energy towards the attending personnel of the apparatus while enhancing the amount of infrared energy that is ultimately directed toward the infant from the reflector 46.

The deflector may be affixed to the insulator 52 by means of a plurality of hangers 58 that suspend the deflector 56 so as to be positioned on the opposite side of the coil 50 with respect to the reflector 46. As a further component, a heat guard 60 is used to protect against the inadvertent contact by the users with the deflector 56 since the deflector 56 can become considerably heated and could be uncomfortable to the touch. The heat guard 60 is preferably made of a material such as aluminum and can be affixed to the deflector 56 by a heat insulating connector such as a rivet 62. In actual use, it has been found that the deflector 56 may reach a temperature of about 200 degrees Centigrade while the heat guard 60 may reach a maximum temperature of about 85 degrees Centigrade.

Turning briefly to FIG. 4, there is shown a cross sectional view of the radiant heater 38 utilizing an alternate infrared energy emitter 64 that may be used with the present invention. In the Fig., the infrared energy emitter 64 comprises a ceramic core 66 that is mounted to the reflector 46 by means of a fastener 68 that may be affixed to the reflector 46 by nut 70. Wrapped about the exterior of the ceramic core core 66 that is mounted to the reflector 46 by means of a fastener 68 that may be affixed to the reflector 46 by nut 70. Wrapped about the exterior of the ceramic core 66 is a resistance wire 72 and which is connected to the source of power by means of electrical wires 74. A quartz tube 78 encircles and encloses the ceramic core 66 and the resistance wire 72 for protection of the overall infrared energy emitter 64. As can thus be seen, the infrared energy emitter 64 can be used as an alternate to the infrared emitter 48 of FIGS. 3A–D and may also include the same deflector 56 and heat guard 60 for the same purposes as previously explained.

Figure 5A:
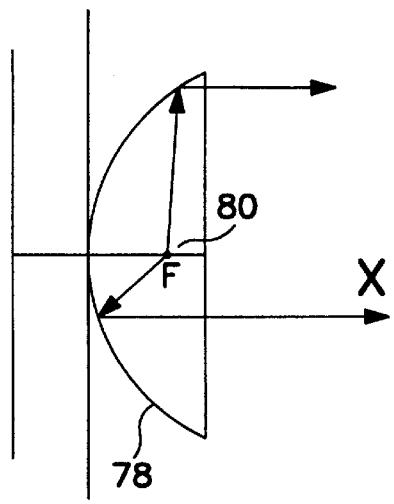
FIG. 5A–5C are schematic views of the configurations of reflectors that are usable with the radiant heater of the present invention.
Figure 5B:
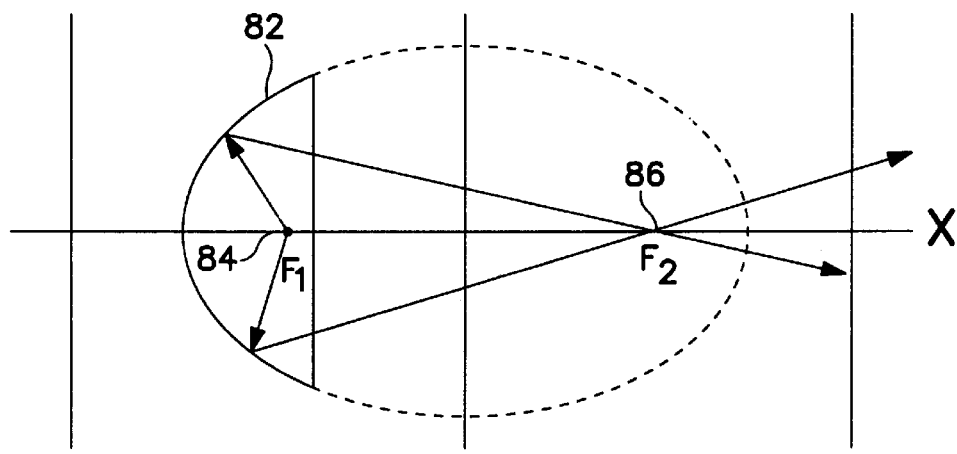
Figure 5C:
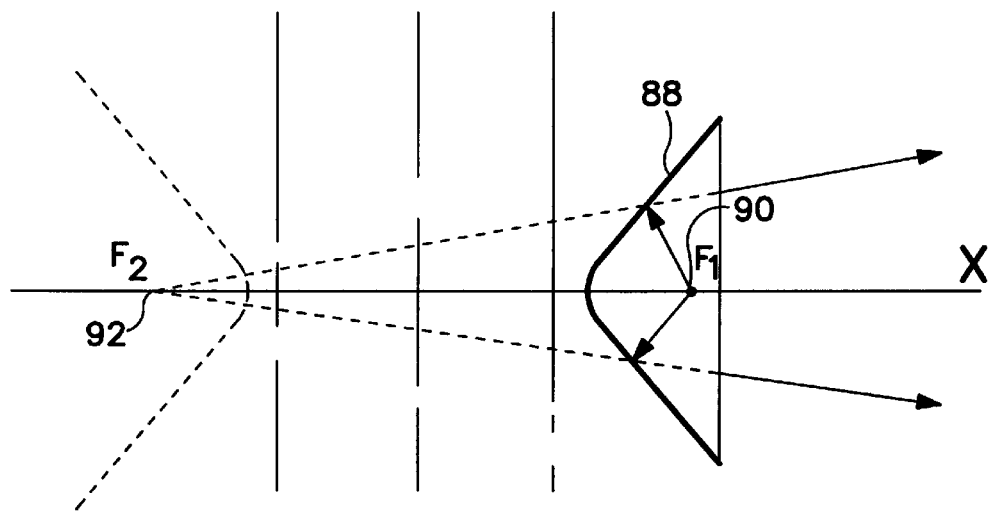

Turning now to FIGS. 5A–5C, there are shown schematics of the shapes that can be utilized for the reflector 46. As indicated, the shapes include a paraboloid reflector 78 as shown in FIG. 5A having a single focal point at 80, a ellipsoid reflector 82 as shown in FIG. 5B having two focal points 84 and 86 and a hyperboloid reflector 88 as shown in FIG. 5C having two focal points 90 and 92. In the case of the paraboloid reflector 78, the ideal position of the infrared emitter is at the focal point 80 and which then reflects the infrared energy toward the infant. In the case of the ellipsoid reflector 82, the ideal position of the infrared emitter is the focal point 84, that is, the focal point closest to the ellipsoid reflector 82 itself. Likewise, with the hyperboloid, the ideal location of the infrared emitter is the focal point 90, again, the focal point closest to the hyperbolic reflector 88. As previously explained, it is the objective to place the infrared emitter actually at the particular desired focal point, however, the emitters are not point sources, as obviously, they have finite dimensions and it in is therefore necessary to position the infrared emitter as close to the particular focal point as it practical and then some adjustment may have to be made to arrive at the desired footprint of the infrared energy that impinges upon the upper surface 24 of the infant bed 22 (FIG. 2).

While the present invention has been set forth in terms of a specific embodiment, it will be understood that the infant care center herein disclosed may be modified or altered by those skilled in the art to other configurations. Accordingly, the invention is to be broadly construed and limited only by the scope and spirit of the claims appended hereto.

I claim:

1. An infant care center comprising:
   a frame;
   a generally planar infant bed affixed to said frame and adapted to underlie an infant;
   a radiant heater affixed to said frame above said infant bed, said radiant heater comprising an infrared emitter and a reflector positioned with respect to said infrared emitter to reflect infrared radiation from said infrared emitter toward said generally planar infant bed, said reflector being formed in the geometric shape selected from the group consisting of an ellipsoid, a paraboloid and a hyperboloid, said radiant heater providing radiant energy to impinge upon said planar infant bed in a substantially uniform pattern.

2. An infant care center as defined in claim 1 wherein said reflector is formed in the geometric shape of a paraboloid having a focal point and said infrared emitter is located substantially at said focal point.

3. An infant care center as defined in claim 1 wherein said reflector is formed in the geometric shape of an ellipsoid or a hyperboloid having two focal points at differing distances from said reflector and said infrared emitter is located substantially at the location of the focal point nearest to said reflector.

4. An infant care center as defined in claim 1 wherein said infrared emitter is a tubular member comprising an outer metallic sheath and a coiled resistance wire contained within said sheath and embedded within an insulating material.

5. An infant car center as defined in claim 4 wherein said insulating material is magnesium oxide.

6. An infant care center as defined in claim 1 wherein said infrared emitter comprises a ceramic core affixed to said reflector, a resistance wire wrapped about the exterior of said ceramic core, and a quartz tube enclosing said ceramic core and said resistance wire.

7. An infant care center comprising:

a frame;

a generally planar infant bed affixed to said frame and adapted to underlie an infant, said planar infant bed shaped as a rectangle having two long sides and two short sides;

a radiant heater affixed to said frame above said infant bed and located substantially above one of said short sides of said planar infant bed, said radiant heater comprising an infrared emitter and a reflector positioned with respect to said infrared emitter to reflect infrared radiation from said infrared emitter toward said generally planar infant bed to impinge upon said planar infant bed in a substantially uniform pattern wherein said reflector is formed in the geometric shape selected from the group consisting of an ellipsoid, a paraboloid, and a hyperboloid.

8. An infrared heater adapted to direct infrared radiation toward a patient, said infrared heater comprising an infrared emitter, a reflector positioned with respect to said infrared emitter to reflect infrared radiation from said infrared emitter toward a patient, said reflector being formed in the geometric shape selected from the group consisting of an ellipsoid, a paraboloid and a hyperboloid, said radiant heater providing radiant energy to impinge upon said patient in a substantially uniform pattern, said radiant heater further including a deflector mounted between said infrared emitter and a patient and adapted to reflect infrared radiation toward said reflector to be reflected by said reflector toward a patient.

9. An infrared heater adapted to direct infrared radiation toward a patient as defined in claim 8 wherein said deflector is generally in the shape of a hemisphere having a truncated end.

10. An infrared heater adapted to direct infrared radiation toward a patient as defined in claim 8 wherein said deflector is mounted to said reflector.

11. An infrared heater adapted to direct infrared radiation toward a patient as defined in claim 8 wherein said deflector includes an insulated member mounted to said deflector to provide a surface that is substantially at a lesser temperature than said deflector.

12. A method of providing heat to a patient positioned upon a patient bed comprising the steps of:

providing an infrared emitter adapted to emit radiation within the infrared spectra above the patient bed; and reflecting radiant energy emitted by the infrared emitter with a paraboloid, ellipsoid or hyperboloid shaped reflector to create a generally uniform pattern of heat on the patient bed.

13. A method of providing heat to a patient as defined in claim 12 further including the step of reflecting some of the radiant energy emitted by the infrared emitter away from the patient bed toward the reflector.

14. A method of providing heat to a patent as defined in claim 12 further including the step of positioning the infrared emitter near one of at least one focal point of the reflector.

* * * * *